(12) United States Patent
Hermanns et al.

(10) Patent No.: US 6,580,813 B1
(45) Date of Patent: Jun. 17, 2003

(54) METHOD AND APPARATUS FOR DETECTING RESIDUAL YARN ON SPINNING COP TUBES

(75) Inventors: Ferdinand-Josef Hermanns, Erkelenz (DE); Andreas Krüger, Mönchengladbach (DE); Harald Müllers, Erkelenz (DE)

(73) Assignee: W. Schlafhorst AG & Co. (DE)

( * ) Notice: Subject to any disclaimer, the term of this patent is extended or adjusted under 35 U.S.C. 154(b) by 0 days.

(21) Appl. No.: 09/370,553

(22) Filed: Aug. 9, 1999

(30) Foreign Application Priority Data

Aug. 10, 1998 (DE) .......................................... 198 36 071

(51) Int. Cl.$^7$ ................................................ G06K 9/00
(52) U.S. Cl. ..................... 382/111; 250/559.4; 242/118; 356/238.2
(58) Field of Search ................................ 382/111, 263; 250/559, 559.4, 223, 559.8; 348/88; 242/412, 118, 118.3, 125, 128, 474.1, 475, 473; 57/243; 28/295, 297; 356/237, 238.1, 238.2, 429; 700/139, 144; 428/36.3

(56) References Cited

U.S. PATENT DOCUMENTS

| | | | |
|---|---|---|---|
| 4,887,155 A | * | 12/1989 | Massen ........................ 348/88 |
| 5,118,958 A | * | 6/1992 | Noshi et al. .............. 250/559.4 |
| 5,179,769 A | * | 1/1993 | Ferguson, Sr. et al. ....... 28/292 |
| 5,212,389 A | * | 5/1993 | Wirtz .......................... 250/559 |
| 5,224,172 A | * | 6/1993 | Masai .......................... 382/111 |
| 5,283,443 A | * | 2/1994 | Norton-Wayne et al. ... 250/572 |
| 5,832,115 A | * | 11/1998 | Rosenberg .................. 382/199 |

FOREIGN PATENT DOCUMENTS

| | | |
|---|---|---|
| CH | 686 779 A5 | 6/1996 |
| DE | 1 278 308 | 9/1968 |
| DE | 2056 577 | 5/1971 |
| DE | 40 10 884 A1 | 10/1990 |
| DE | 41 24 750 A1 | 1/1992 |
| DE | 40 12 462 C2 | 4/1992 |
| DE | 41 10 626 A1 | 10/1992 |
| DE | 42 11 985 A1 | 10/1992 |
| DE | 42 17 059 A1 | 11/1992 |
| DE | 40 10 884 C2 | 3/1993 |
| DE | 41 31 664 A1 | 3/1993 |
| DE | 43 23 547 A1 | 1/1994 |
| DE | 44 06 324 A1 | 9/1995 |
| DE | 195 01 204 A1 | 9/1995 |
| DE | 40 08 795 C2 | 5/1996 |
| DE | 196 42 712 A1 | 4/1998 |
| DE | 196 43 406 A1 | 4/1998 |
| DE | 197 00 352 A1 | 7/1998 |
| EP | 402 731 B1 | 9/1993 |
| JP | 54-30943 | 7/1979 |
| JP | 63-107370 | 5/1988 |

\* cited by examiner

*Primary Examiner*—Bhavesh M. Mehta
*Assistant Examiner*—Abolfazl Tabatabai
(74) *Attorney, Agent, or Firm*—Kennedy Covington Lobdell & Hickman, LLP

(57) ABSTRACT

A method and apparatus of detecting residual yarn on spinning cop tubes, wherein a spinning cop tube is exposed to a suitable light source; the light reflected by the spinning cop tube is detected by a suitable means, e.g., via a camera or other picture-taking device, and two-dimensional picture signals of the spinning cop tube are generated thereby on the basis of the reflected light detected in order to generate a picture matrix comprising picture data in digital form; and the picture signals thusly generated are evaluated by means of performing an edge filtering of the digital picture data in order to segment image edges corresponding to brightness transitions in the picture matrix, from which the presence of residual yarn on the spinning cop tube can be assessed based on the edge filtering.

32 Claims, 4 Drawing Sheets

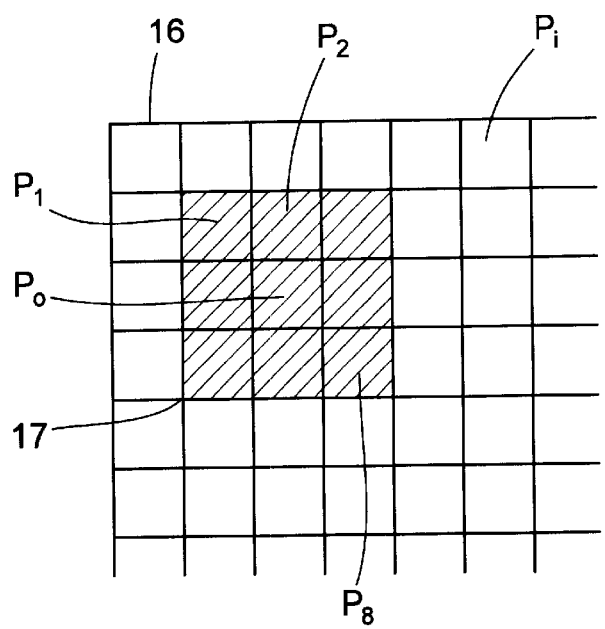
FIG. 4
FIG. 5a
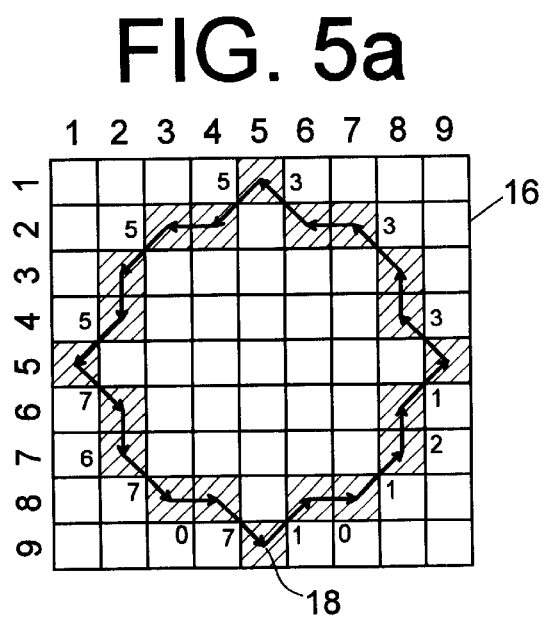
FIG. 5b
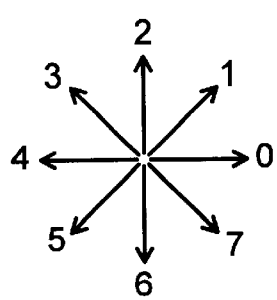
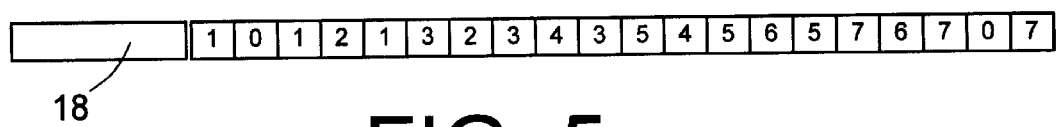
FIG. 5c

ମETHOD AND APPARATUS FOR DETECTING RESIDUAL YARN ON SPINNING COP TUBES

BACKGROUND OF THE INVENTION

The present invention relates to a method and a corresponding apparatus for detecting residual yarn remaining on spinning cop tubes, for use in automatic bobbin winding machines.

Modern spinning machines have a high output of spinning cops, and so more stringent demands are made of the processing capacity of the spinning machines downstream as well.

It is also necessary for the unwound tubes to be returned in adequate quantity to the spinning machine. To assure a high degree of automation, closed transport loops in the region of the spinning machine and optionally direct coupling of automatic bobbin winding machines to the spinning machines are therefore widely used.

In modern automated textile production facilities, the spinning cop tubes are thus subject to a circulatory process. The flow of material in such a closed spinning cop and tube transport system in the prior art, as known for instance from European Patent Disclosure EP 0 402 731 B1, is shown schematically in FIG. 6. Once the yarn has been made in a ring spinning machine, the resultant spinning cop is automatically delivered to the bobbin winding machine, where the cop is mounted on a cop carrier. Via conveyor belts, the spinning cop is transported from the mounting station to a cop preparation station 4, so that the end of the yarn can be separated thereby and made ready for being securely grasped later. The spinning cop then moves into a winding station 1, where the winding process is performed.

However, it can happen that the bobbin winder loses the beginning end of the yarn on the spinning cop in place, especially if the yarn breaks. After a few failed attempts at splicing, the spinning cop tube is treated as being presumably empty and is finally ejected from the spinning station 1. Thus, it is not assured that the ejected spinning cop tubes are in fact always empty. On the contrary, the ejected spinning cop tubes differ in terms of how much yarn remains on them and accordingly their reprocessing must be different.

To automate the winding process, it is therefore necessary to determine the status of the spinning cops shunted out of the winding station 1, so that individual residual yarn windings remaining on the cop tube or a possibly full or otherwise usable amount of residual yarn remaining on the spinning cop tube can be detected reliably. To that end, in the transport system shown in FIG. 6, an electromechanical tube monitor 2 is provided, which detects the amount of residual yarn remaining on the spinning cop tube.

The tube monitor 2 can be designed in the form of an electromechanical sensor (see for instance German Patent Application DE 41 10 626 A1), in which a metal comb sweeps laterally over the spinning cop tube. Depending on how far this comb can sweep over the tube, conclusions can be drawn as to the remaining quantity of yarn on the spinning cop tube. Spinning cops that have been completely unwound, i.e., empty tubes, are automatically transported back to the spinning machine to be refilled. Conversely, if a residual yarn remaining on the spinning cop tube has been detected by the tube monitor 2, then for instance with the aid of shunts the transport direction of the applicable spinning cop tube is diverted such that the spinning cop tube is delivered over a secondary route to a tube cleaning device 3.

This tube cleaning device 3 has the task of removing the remaining yarn from the spinning cop tube. To that end, the yarn package is optionally cut open and then stripped off the spinning cop.

However, since it can also happen that the residual yarn remaining on the tube can still be reused and thus can be delivered to the spinning station 1 again, the tube monitor 2 also provides a statement as to whether the remaining yarn quantity detected on the spinning cop tube is sufficient to be reused. If so, then the spinning cop tube is not delivered to the tube cleaner 3 but rather is transported to the cop preparation unit 4, which in turn grasps the beginning of the yarn on the spinning cop and after placing this beginning end of the yarn at a predetermined point delivers the spinning cop to a winding station 1.

Instead of the design shown in FIG. 6, in which the tube monitor 2 serves as a multifunction sensor that can distinguish between empty tubes, tubes with a slight residual yarn, and tubes with a still usable residual yarn, it is also possible at the position of the tube monitor 2 to provide a first sensor, which detects merely whether a residual yarn is or is not present on the spinning cop tube. In that case, before a branching point toward the tube. cleaner 3, a further sensor is provided, which finally distinguishes whether or not the remaining residual yarn is sufficient for reuse and, by suitably controlling the transport route as a function of this decision, delivers the spinning cop tube either to the cop preparation station 4 or the tube cleaner 3.

As already explained above, in the bobbin winder shown in FIG. 6 an electromechanical spinning cop feeler in the form of a metal comb may be used as the tube monitor 2, but this has multiple disadvantages. For instance, in this design, the tube monitor 2 must be readjusted by hand for different types and sizes of spinning cop tubes. The metal comb can also wear down over time, and individual remaining yarns are not removed from the spinning cop tube but are instead merely pushed downward by the metal comb, so that these remaining yarns become tangled with the new yarn in an ensuing spinning process and thus can cause the ring spinning spindle to stop. It is also disadvantageous that the mechanical feeler elements of the sensor can damage the yarn, particularly fine yarns.

Japanese Patent Disclosure JP 63-107370 describes a similar mechanical sensor for detecting remaining yarns on spinning cop tubes. According to this reference, a rotatably supported mechanical arm is moved from top to bottom along the spinning cop tube and, depending on the degree to which the spinning cop tube is filled with yarn, the rotatably supported arm can be deflected to a variable extent. The deflection of the arm is detected with the aid of a suitable sensor, in order to draw conclusions as to any possible remaining yarn windings on the spinning cop tube.

In addition to the above-described detection of residual yarns on spinning cop tubes with the aid of mechanical sensors or feelers, devices are also known that detect remaining yarn or residual yarns on spinning cop tubes in contactless fashion.

To this end, German published examined Patent Application DE-AS 1 278 308 proposes irradiating the spinning cop tube with the aid of a light source such that the light reflected by the spinning cop tube may be detected with the aid of a photocell. The beam of light reflected from the spinning cop tube affects the photocell more or less, depending on whether a winding residue is or is not present on the spinning cop tube. During the scanning operation, a relative motion always occurs between the spinning cop tube and the photocell acting as a sensor, i.e., the spinning cop tube is moved horizontally past the photocell.

It is furthermore known from German Patent DE 40 08 795 C2, which defines the generic starting point for the present invention, to detect residual yarn remaining on a spinning cop tube by scanning the spinning cop tube with the aid of a relative motion between the spinning cop tube and a sensor, while the spinning cop tube is being transported in an upright disposition; the sensor is mounted on a stationary lifting divide, with the aid of which it is moved along the spinning cop tube with an approximately constant spacing from the surface of the tube. In particular, the sensor may be a photosensor, which evaluates light shone at a certain angle from the vertical onto the surface of the spinning cop tube and reflected back by the spinning cop tube, so as to detect residual yarns on the spinning cop tube.

Finally, Japanese Patent Disclosure JP 54-30943 also teaches contactless bobbin scanning. The apparatus disclosed in this reference is used to check sliver bobbins, in order to be able to check the exterior of the sliver bobbins for surface flaws, and so forth. The scanner proposed in this reference includes a light source, whose light is projected onto the sliver through a slit, designed and disposed to correspond to the comb line of the sliver bobbin. A television camera scans the sliver bobbin. In particular, the television camera scans the sliver bobbin line by line and on the basis of a comparison with reference values ascertains the quality of the sliver bobbin, so that bumps, winding gaps, and so forth in the sliver bobbin can be found. This apparatus is not, however, used to detect residual yarns or remaining yarn on spinning cop tubes.

SUMMARY OF THE INVENTION

It is accordingly an object of the present invention to create a method and a corresponding apparatus for detecting residual yarns on spinning cop tubes in which more certain and reliable detection of residual yarns is possible. With the aid of the present invention, it should also be possible not only to detect residual yarns but also to draw reliable conclusions about the degree to which the spinning cop is filled with residual yarn, so that if the spinning cop has reusable residual yarn it can be returned to a winding station, optionally after passing through a spinning cop preparation apparatus for finding the leading end of the yarn.

The above object is attained in accordance with the present invention by a method and apparatus of detecting residual yarn on spinning cop tubes, wherein a spinning cop tube is exposed to a suitable light source; the light reflected by the spinning cop tube is detected by a suitable means, e.g., via a camera or other picture-taking device, and two-dimensional picture signals of the spinning cop tube are generated thereby on the basis of the reflected light detected in order to generate a picture matrix comprising picture data in digital form; and the picture signals thusly generated are evaluated by means of performing an edge filtering of the digital picture data in order to segment image edges corresponding to brightness transitions in the picture matrix, from which the presence of residual yarn on the spinning cop tube can be assessed based on the edge filtering. The preferred, advantageous forms of embodiment of the present invention, described more fully hereinafter, contribute to the best possible scanning of the spinning cop tubes and the simplest possible, yet still reliable evaluation of the information obtained in the process.

Also in accordance with the present invention, residual yarns are detected in contactless fashion, yet digital picture signals are generated which can be subjected to digital image processing. In order to obtain object contours of the spinning cop tube to be examined from the digital picture data, an edge filter algorithm is employed, with the aid of which edges in the pictured image, i.e., transitions between brightness or gray values, can be emphasized or enhanced in the digital picture matrix. On the basis of the object contours thusly obtained, a reliable assessment of the yarn winding status of the applicable spinning cop tube is possible, so that in particular slight residual yarns on the spinning cop tube can be detected, and if greater residual yarn quantities are present, it can be assessed whether the package remainders thus detected can be reused.

The region of a spinning cop tube to be checked is as a rule the entire region which in a fully wound cop carries the yarn windings. However, it may also suffice to check only the lower third of the tube, which is where residual yarn is most likely to remain.

Scanning the spinning cop tube can be done in the present invention, particularly during transport of the spinning cop tube, in the form of a snapshot made by a full-frame camera. This camera may in particular be a CCD video camera, and a black and white picture suffices. To improve the picture utilization, or in other words to attain higher image resolution, optical distortion can be provided via a cylindrical optical element or concave mirror. Rotating the camera 90 degrees about its optical axis also contributes to higher image resolution. With the aid of a picture converter, the picture signal furnished by the video camera can be digitized and made available to a downstream evaluation computer, for instance in the form of a conventional personal computer. There, the picture is analyzed with a specially developed evaluation algorithm from which a reliable conclusion may be made about the yarn winding status of the specimen examined.

Instead of a CCD video camera, a digital still camera can also be used to scan the spinning cop tubes; in such a digital still camera, the digitization of the picture taken is done internally in the camera, so that later digitization using a picture converter is unnecessary.

A specimen is advantageously illuminated using a light source that projects diffused light. Such a light source can for instance comprise a plurality of arrays of ultra-bright light-emitting diodes (LEDs). These LED arrays are disposed such that the edges and contours of the spinning cop are enhanced or emphasized and no disturbing reflection occurs. The long service life, sturdiness and low power consumption of LEDs are advantages. By mixing the colors of the LEDs (red, green and yellow), the color spectrum can be widened. By using a diffuser, for instance in the form of a ground-glass plate or diffusing lens or screen, homogeneous illumination of the particular specimen can be achieved despite the intrinsically point-wise projection characteristic of LEDs. The disposition of the LEDs should advantageously be such that total reflection of the light from these LEDs to the applicable camera or other picture-taking device cannot occur. Instead of the use of different-colored LEDs, white LEDs that have recently become increasingly available on the market can also be used.

The digital image processing performed according to the present invention is based substantially on the extraction and analysis of the object structures of the applicable specimen, in particular the edges of the tube, the yarn layers, and the specific characteristics of the tube. To improve the contrast between the background, the spinning cop tube and the yarn windings, the digital picture matrix can be alternatingly squared, scaled back, and finally added back again to the original picture matrix. For edge filtering, Sobel's filter algorithm can particularly be employed; the picture data thus processed are then binarized with the aid of a dynamic threshold value. For the sake of the most exact possible enhancement of the picture matrix, the object contours obtained by processing the picture data in this manner can subsequently be thinned with the aid of an erosion process with ensuing finding of the difference and, finally, the contour edges of the spinning cop tube being examined are extracted with the aid of a special edge tracing method, for instance by applying the Freeman chain code. The interpretation of the object contours extracted in this way is then done by assessment of their geometric shape or alternatively by a comparison with a reference picture of a comparison spinning cop tube.

In the picture taking method according to the present invention, it is not necessary for the applicable specimen to be stopped in front of the picture-taking device. That is, the detection of remaining yarn is advantageously done while the applicable spinning cop tube is moving past the picture-taking device.

The invention is described below in further detail with reference to a preferred exemplary embodiment in conjunction with the accompanying drawings.

BRIEF DESCRIPTION OF THE DRAWINGS

FIG. 4 is a schematic diagram illustrating and explaining the mode of operation of the edge filtering of a picture matrix performed in accordance with the present invention;

FIGS. 5a, 5b and 5c are schematic diagrams illustrating and explaining the edge tracing method, employed in a preferred exemplary embodiment of the present invention, by applying the Freeman chain code.

DETAILED DESCRIPTION OF THE PREFERRED EMBODIMENT

Figure 1:
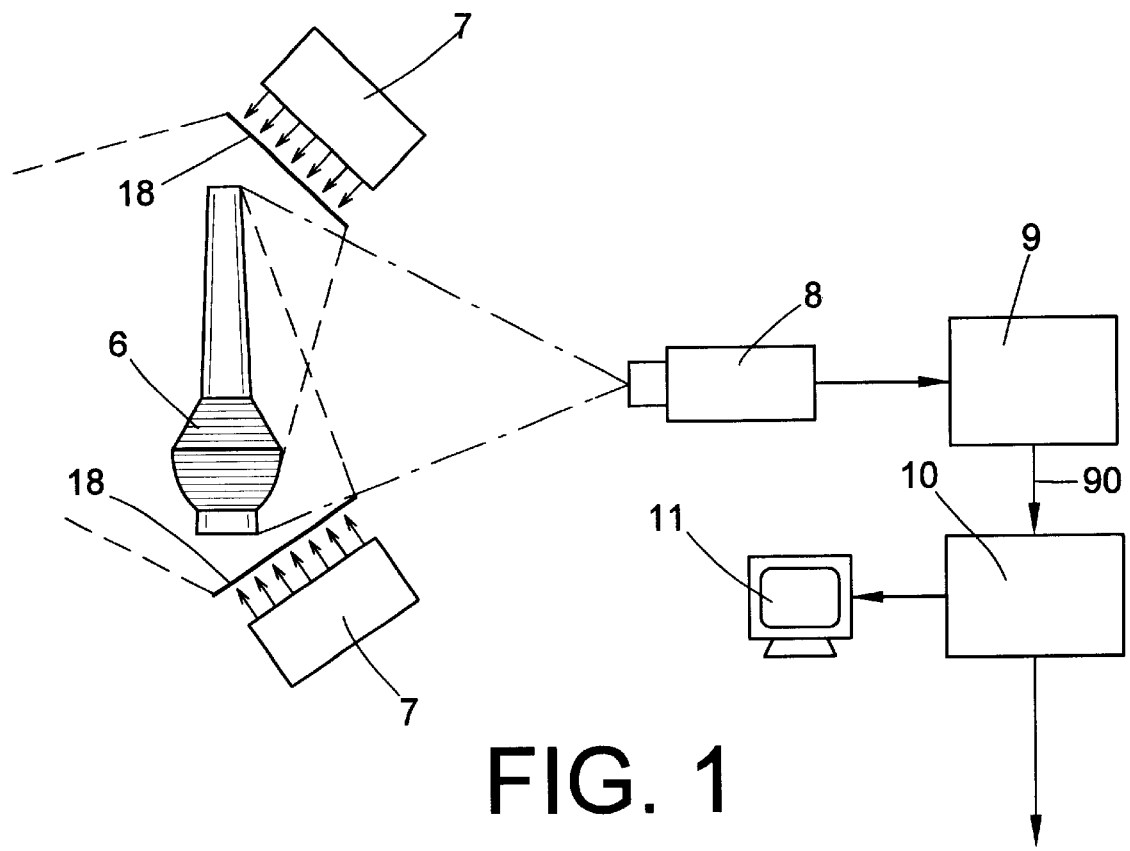
FIG. 1 is a schematic diagram showing the layout of an apparatus according to the present invention for detecting residual yarns on spinning cop tubes.
Figure 6:
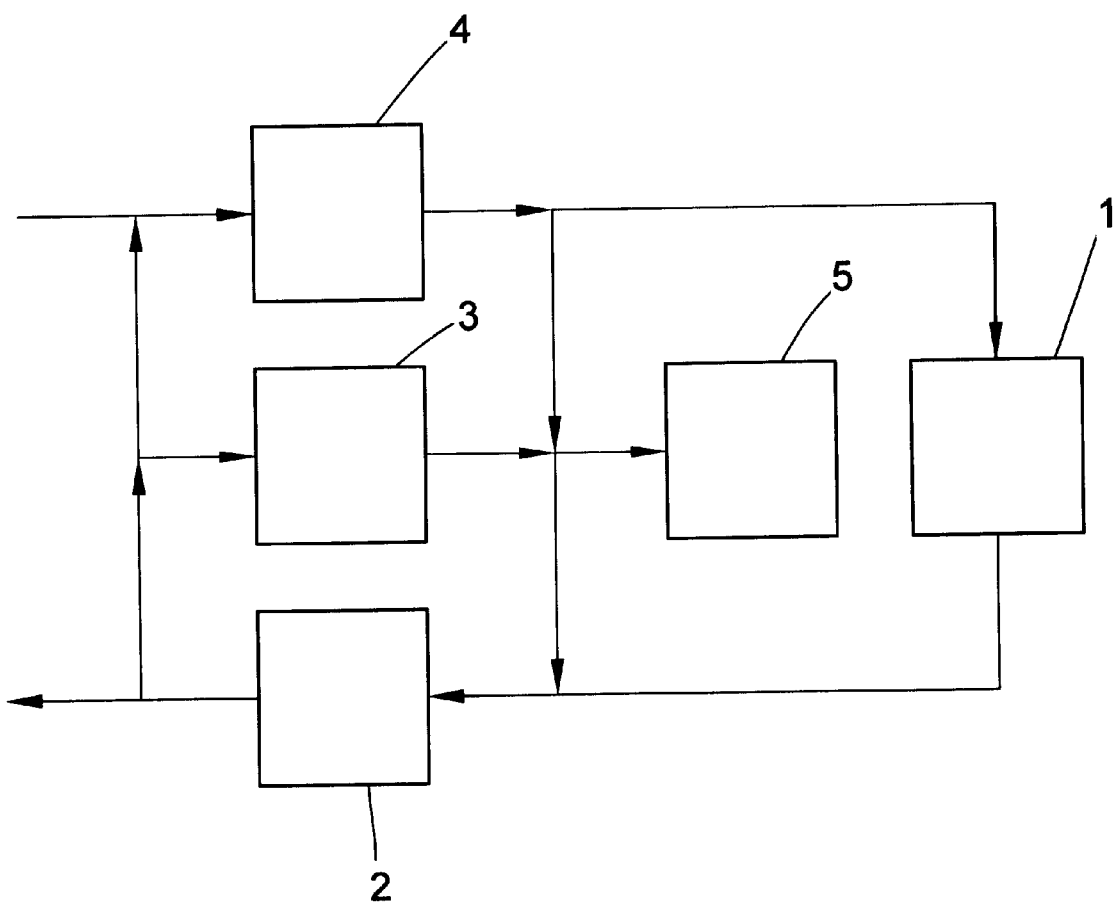
FIG. 6 is a schematic diagram illustrating and explaining the transport routes of spinning cop tubes in an automatic bobbin winding machine.

Referring now to the accompanying drawings and initially to FIG. 1, an apparatus for detecting residual yarns on a spinning cop tube 6 according to the present invention is schematically shown, and basically includes at least one light source 7, which exposes the spinning cop tube 6 to diffuse light. The spinning cop tube 6 is preferably being transported in a conveyor system associated with an automatic bobbin winder such as depicted in FIG. 6 discussed above. A picture-taking device such as camera 8, in particular a CCD video camera, scans the thusly exposed spinning cop tube 6 and furnishes a corresponding video or picture signal to a downstream picture converter 9, for instance in the form of a frame grabber, wherein the signal is converted into digital picture data 90 that are delivered to a computer 10. The computer 10 subjects the digital picture data 90 to digital image processing and thus evaluates the digital picture data 90 in order to obtain information and to draw conclusions on the residual yarn winding status of the applicable spinning cop tube 6, i.e., the presence and amount of any such residual yarn. A picture or image corresponding to the applicable spinning cop tube 6 can be shown on the monitor 11 of the computer 10. Once the computer 10 has ascertained the presence and amount of any such residual yarn on the spinning cop tube, the conveyor belt controller, for instance of the transportation system shown in FIG. 6 for an automatic bobbin winder, is triggered in order to adjust the transport route for the spinning cop tube 6 as a function of the detected residual yarn winding status of the spinning cop tube 6. That is, a spinning cop tube 6 with reusable residual yarn is delivered to the cop preparation unit 4 shown in FIG. 6, while a cop 6 with a residual yarn that cannot be reused is delivered to the tube cleaner 3. A spinning cop tube 6 detected as being empty is transported directly to the spinning machine rather than being delivered to the cop preparation unit 4 or the tube cleaner 3.

In the arrangement shown in FIG. 1, it is possible in particular for a plurality of light sources 7 to be disposed laterally of the spinning cop tube 6 to be examined, in such a way that they illuminate the spinning cop tube 6 as evenly as possible. Each light source 7 can be embodied in the form of one or more arrays of LEDs, as will be described in further detail hereinafter. In order to scatter the light of such LEDs, which is projected in point form or aimed form, and thus to make possible more even exposure of the spinning cop 6, a diffuser 18, for instance in the form of a ground-glass plate or a diffusing lens or screen, is disposed in front of the LEDs.

For implementing the apparatus shown in FIG. 1 in a bobbin winder, all the problematic external influences must be minimized. These include different light connections, possible vibration of the machine, or floating dust and fibers inside the production facility. The spinning cop tubes 6 are transported on a carrier through a housing with an inlet and exit opening and, at a predefined position inside the housing, the cop tubes 6 are moved past the camera 8. By means of the cladding of this housing, the internal light conditions can be distinguished from external light conditions, and soiling of the camera lens can be reduced. To prevent floating dust inside the picture-taking surroundings, a fan can be employed which feeds prefiltered air into the housing continuously through a further opening. This creates an overpressure in the housing, and as a result the dust particles are blown out of the housing. The camera is preferably mounted in vibration-damped fashion, to avoid blurring caused by machine vibration.

With the aid of inductive proximity switches, for example, it can be ascertained that the picture-taking position has been reached by a spinning cop tube 6. If such a switch is tripped by a spinning cop tube 6 moving past, the camera 8 is accordingly signaled so that the picture is taken by the camera 8. The spinning cop tube 6 is immediately advanced out of the picture-taking surroundings to the next branching point of the conveyor belt. The time between when the picture is taken and when the next branching point is reached is enough for the computer 10 being used to filter and analyze the information obtained by the picture taking, so that at the next branching point the spinning cop tube can be either ejected, placed in front of another winding station 1 by way of the cop preparation unit 4 shown in FIG. 6, or transported to the tube cleaning station 3, depending on the results of the picture evaluation. At the branching points of the respective conveyor belt, shunts in the form of electromagnetic positioning devices can be provided for this purpose and are triggered in accordance with the information furnished by the computer 10 regarding the residual yarn winding status of the particular cop tube specimen 6 being examined. Since the picture taking is done as the spinning cop tube 6 travels past, no down times are brought about during the transporting of the spinning cop tube 6. The bobbin winder can thus be optimally utilized, and the throughput can be increased.

By using digital picture processing as proposed in the present invention, the problems described at the outset involved in conventional detection of residual yarns on spinning cop tubes can be overcome and, with the aid of a relatively simple construction and economical means, a reliable conclusion can be made about the residual yarn winding status of a given cop tube specimen 6.

The light sources 7 shown in FIG. 1 will now be described in further detail. The object of the illumination employed in FIG. 1 is to enhance or emphasize the relevant information on the cop 6 of which the picture is to be taken and to suppress nonrelevant information. As the light source 7, light-emitting diodes (LEDs) can be used in particular, because they are the most energy-saving, long-lived and economical alternative lighting means. To widen the color spectrum of the lighting, LEDs in the colors red, yellow and green are preferably mixed in arrays. This makes the lighting overall less vulnerable to color-absorbing properties of the spinning cop tube 6 and the residual yarns that may be present.

Figure 2:
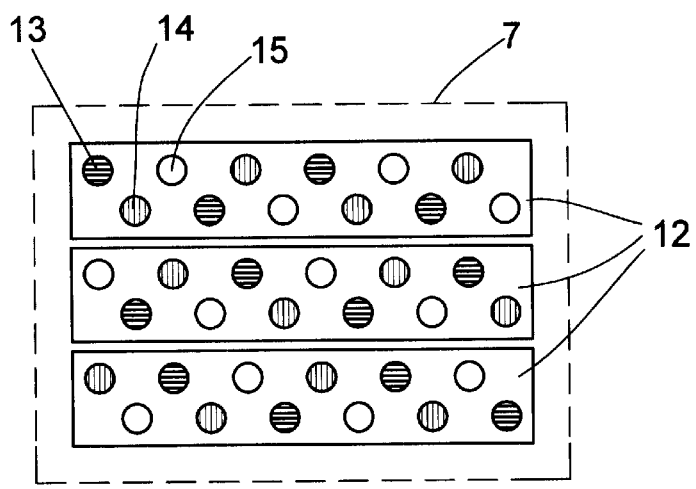
FIG. 2 shows an example of the layout of the light source used in FIG. 1.

FIG. 2 as an example shows the layout of a light source 7 shown in FIG. 1. In FIG. 2, the light source 7 may have a plurality of lighting units 12, each for instance formed by perforated raster cards onto which the LEDs of a different color are soldered in a matrix pattern as shown in FIG. 2. By means of the mutually offset arrangement of the green, yellow and red LEDs 13, 14, and 15, respectively, the lighting of the spinning cop can be made to approximate the spectrum of white light. Instead of using LEDs 13 through 15 of different colors, white LEDs, which are recently increasingly available on the market, can also be used. To avoid reflection toward the camera 8 shown in FIG. 1, it is advantageous to dispose the individual light sources 7 laterally of the applicable cop tube specimen 6, in such a way that the beams of light from the light sources 7 cannot directly strike or be reflected onto the lens of the camera.

As has already been explained, a CCD (Charged Coupled Device) camera is particularly appropriate as the picture-taking device. Such CCD cameras use CCD image sensors, which with the aid of radiation-sensitive surfaces convert optical picture information into electrical information by utilizing the photo effect at the radiation-sensitive surface. CCD picture sensors of this kind are disposed in lines or matrixes in surfaces, and the charge generated in a CCD sensor by incident light is carried onward into an adjacent sensor element until all the charges generated during a phase of exposure to light have been carried into a readout register and from there into a picture memory.

In this way, the CCD camera 8 furnishes an analog video or picture signal that is provided with synchronizing pulses; this signal must be digitized for the ensuing digital picture processing. This is done with the aid of the picture converter 9, already shown in FIG. 1, which may for instance be formed by a frame grabber card installed in the evaluation computer 10 that digitizes the picture signal furnished by the CCD camera 8, so that the picture taken can be shown on the monitor 11 of the computer 10 as a real-time video image.

The CCD camera 8 is preferably operated in what is known as the interlaced mode, to prevent a moire effect from occurring; that is, the camera 8 successively generates two half-frames, and the first half frame is composed of even-numbered lines while the second half-frame is composed of odd-numbered lines. A black and white two-dimensional camera is advantageously used as the CCD camera 8 and shows the picture it has taken in the form of shades of gray. Such black and white cameras are distinguished by their relatively low cost and their high reliability. It is also conceivable to use a digital still camera, since only still pictures have to be taken of a cop tube specimen 6. In that case, the downstream picture converter 9 can be dispensed with, since the digital still camera already furnishes digital picture data.

One particular problem which may occur in the picture taking is due to the ratio of the sides of the spinning cop tubes. The ratio between the height and the width of an average spinning cop tube is approximately 1:8, while commercially available CCD two-dimensional cameras have an aspect ratio of 4:3, based on the European television standard. In order to compensate at least in part for this inadequacy, it is advantageous to rotate the CCD two-dimensional camera 90 degrees about its optical axis. By the additional use of a concave mirror or cylindrical optical element, the ratio of the length to width of the spinning cop tube in question can also be adapted with respect to the optical image or distorted in such a way that more of the area of the gate of the CCD camera 8 can be utilized.

The picture converter 9 can be designed such that it converts the picture information supply to it directly into a matrix of shades of gray and a particular graphic format (size and/or orientation, e.g., portrait or landscape). The digital picture data 90 thusly generated are then delivered to the computer 10 for subsequent image processing. The picture data are buffer-stored in particular on the hard disk of the computer 10 for the sake of access to them afterward via the working memory. As the graphic format of the digital picture data, a raster format is particularly appropriate. In the vector graphics, an image in the form of vectors is stored in the memory and calculated from these vectors. All geometric shapes can be composed from simple basic elements, which in turn are calculated by simple mathematical aids.

Figure 3:
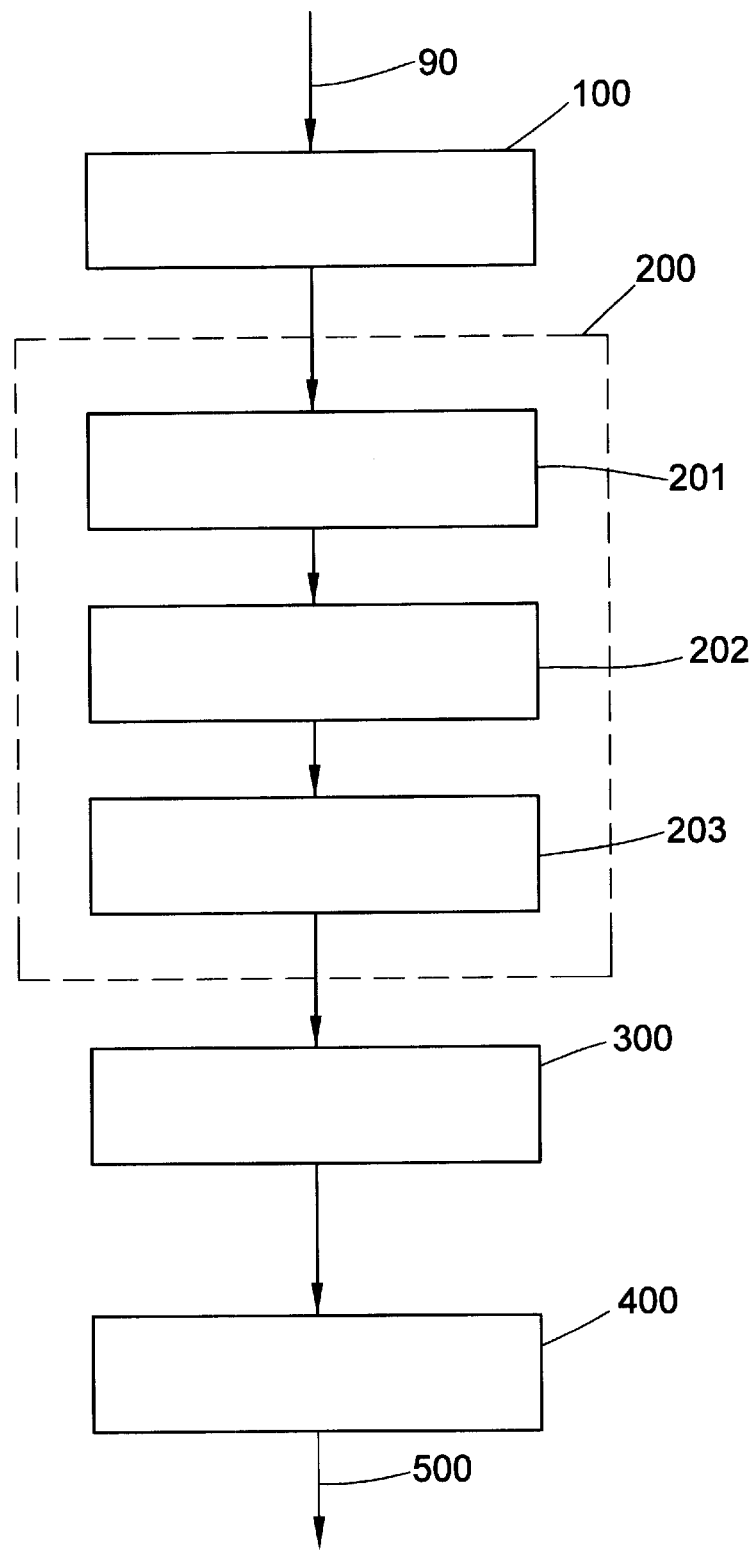
FIG. 3 is a schematic diagram illustrating and explaining the sequence of digital image processing in the apparatus shown in FIG. 1.

The digital image processing, performed by the computer 10, for detecting residual yarns on whichever cop tube specimen 6 is being examined will now be explained in further detail in conjunction with FIGS. 3–5. FIG. 3 shows the general sequence of the digital image processing in the computer 10. Once the digital picture data 90 have been obtained, a contrast enhancement 100 is first performed, in order to increase the gray-value transitions between the spinning cop tube and the remaining yarns. The purpose of this contrast enhancement is thus to more sharply distinguish bright regions from dark regions, to make the ensuing edge filtering more effective. To improve the contrast, first the lowest gray value occurring in the picture matrix is subtracted in every gray value in the picture matrix, and the result is squared pixel by pixel, so that brighter pixels can be more clearly distinguished from darker pixels. Next, the result is adapted to the possible values range or, in other words, is scaled back. The bright yarns are more clearly distinguished from the spinning cop tube, yet the edge of the tube fades relative to the background. To compensate for this disadvantage, the original image, that is, the original picture matrix, is added to the squared picture matrix.

Enhancement, or in other words the emphasizing of the particular object in the thus-obtained revised picture matrix, is then done. The enhancement 200 substantially includes three different processing steps. First, with the aid of edge filtering, the gray value transitions in the picture matrix are emphasized (step 201). Next, the thusly-obtained picture is binarized (step 202). Finally, the contours are thinned (step 203), in order to obtain edges that are not as thick (step 203).

The simplest way of emphasizing objects in a picture matrix is to identify the edges and, as a result, an enhancement of the gray value transitions is done between the background and the actual object. The entire picture matrix is filtered by placing a filter core symmetrically around a pixel currently to be processed and then sliding it line by line from left to right over the entire picture matrix. For the sake of clarification, FIG. 4 shows an example of a picture matrix 16 with many pixels $P_i$. In FIG. 4, a filter operation window 17 corresponding to a certain so-called local operator is shown shaded; it is placed over a pixel $P_0$ to be currently processed and is then slid over the entire picture matrix 16. By using such local operators, conclusions can be made about the direct vicinity of a pixel; that is, in the case shown in FIG. 4 in particular, by the use of such a local operator, conclusions about the ratio of the gray value stage associated with the pixel $P_0$ to the gray value stages or brightness stages associated with the adjacent pixels $P_i$ through $P_8$ can be obtained.

The most commonly used edge filter operator, because it yields good results in the majority of applications and has a reasonable transit time performance, is the so-called Sobel operator; once it has been used, statements are obtained about the gray stage gradients of the various pixels relative to the pixels adjacent to them. The gradients calculated by this edge filtering are stored in memory in the computer 10, and the gradients are in particular buffer-stored separately from the original digital picture data 90. For the sake of an optimal transit time performance, it is recommended that the adjacent pixels of a pixel to be processed in the picture matrix be addressed with pointers. The gradients are calculated by the Sobel's filter algorithm in three steps. First, the values of the pixels disposed adjacent to the pixels to be processed are multiplied by the coefficients of the Sobel filter core in the horizontal and vertical search direction. Next, the sums are each added up in the vertical search directions, and finally the amounts of the two sums calculated in the previous step are added together.

As has already been explained above, the thusly edge-filtered gradient pattern is binarized for further processing (see step 202 in FIG. 3). Each point in the filtered picture matrix is compared for this purpose with a threshold value. If the gradient is above this threshold value, then it contains information; conversely, if it is below the threshold value, it does not contain information. A binarized initial picture with either set or unset pixels is thus obtained. The fundamental threshold value is defined on the basis of the values range for the individual gradients, or in other words as a function of the distance between the greatest and the least gradient. If a static threshold value is used, the problem can arise that information is lost if too high a threshold value is selected, while if the threshold value is overly low, the picture is misleading. In low-contrast regions of the picture, the contours are also more poorly visible than in high-contrast zones. It is therefore advantageous to use a dynamic threshold value, which is calculated individually for each pixel on the basis of the gradient pattern. To calculate the dynamic threshold value, the mean values of the pixels adjacent to a pixel to be processed are ascertained from the gradient pattern and added to one-fourth the gradient values range. Half of this value, finally, produces the dynamic threshold value. If for instance the mean value of one region drops because it is underexposed, then the threshold value drops correspondingly as well, so that good results can always be obtained.

The consequence of the binarization performed in step 202 (see FIG. 3) is data reduction, since in contrast to the original picture of various stages of gray (with 8 bits per pixel, for instance), after binarization each pixel can be memorized using only one bit (to represent either black or white).

As a consequence of the Sobel's filter algorithm described above, the edges emphasized with its aid appear quite thick. These edges should therefore be thinned by the step of contour thinning 203 shown in FIG. 3. This can be done for instance by what is known as erosion. The erosion causes the objects or structures emphasized by the edge filtering to shrink; that is, the edges obtained by the gradient operation that look thick are narrowed by comparison with the neighboring and background pixels. To that end, the value of one object pixel currently to be processed is for instance compared with the values of the adjacent pixels. If the value of one of the neighboring pixels is less than the value of the object pixel, then the neighboring pixel can only be part of the background (assuming a binary image). To make the object shrink, the value of the object pixel is therefore set to the background value. One positive aspect of erosion is that noise components that may possibly be contained in a binary image are also suppressed.

The thinning of the contour regions effected by the erosion leads, however, to the problem that inadequately detected edges are suppressed still further, and thus gaps can appear in the contours. This problem can be overcome by additionally finding a difference between the picture produced by the erosion and the edge-filtered binary image, so that thinned contour regions that are complete in every case are obtained.

After the conclusion of the enhancement 200, or in other words after the edges or contours of the picture taken by the camera 8 of the applicable cop tube specimen 6 have been delineated, conclusions must then be made about the actual picture content, on the basis of the geometric shape of the contours thus obtained. In other words, from the picture matrix obtained by the digital picture processing, the relevant information must be combined into characteristics, to allow drawing conclusions as to the image content from them (characteristic extraction). The characteristic extraction 300 can in principle proceed in two steps. First an edge tracing is performed, in order to ascertain the coherent neighboring pixels beginning at a starting pixel. From the contour fragments thus ascertained, the ones that clearly belong together are then joined together.

For the edge tracing, the Freeman chain code is for instance suitable; this will be explained below in conjunction with FIGS. 5a–5c. As shown in FIG. 5a, beginning at the starting pixel 18 in column 5, line 9, of the picture matrix 16, the neighboring area of the matrix is searched for set neighboring pixels. Once a set neighboring pixel has been found, the position of the starting pixel 18 and the direction from the set neighboring pixel found are stored in memory, and then the search continues from the neighboring pixel that has just been found. In FIG. 5a, the process for finding an edge of an object within a picture matrix 16 is shown as an example. As a key to the coating, the chain code "Windrose" shown in FIG. 5b is used, in which, beginning at the starting pixel, a certain value is assigned to each direction. Thus if beginning at a set starting pixel, a set neighboring pixel immediately to the right of the starting pixel is found, then the value "0" is stored in memory. Conversely, for a set neighboring pixel directly vertically above the starting pixel, the value "2" is stored in memory, and so forth. In FIG. 5c, the memory content corresponding to the contour or edge tracing of FIG. 5a is shown; the individual memorized values each designate the direction, corresponding to the contour course, from a starting pixel to a set neighboring pixel. The edge found from the indications "starting pixel", "ending pixel", and the "directions to the neighboring pixels" can subsequently be reproduced.

Once the contours or contour fragments contained in the picture that has been taken have been ascertained with the aid of step 300 (see FIG. 3), those contour fragments that clearly belong together still must be joined up. For instance, if the starting value of one edge is immediately next to the final value of a further edge, it can be assumed that these two edges form a common contour. The surroundings of each value of one edge are therefore searched for an adjoining edge, so that contour fragments found can be joined up. During this step, those edges that are no longer needed in the subsequent analysis of the information, such as fragments classified as the object periphery, for instance, and which have their starting value in the picture matrix after the last edge classified as a yarn, can be deleted during this step. Thus color markings on the tube, which could have an influence on the assessment, can be eliminated.

After the characteristic extraction 300, analysis 400 ensues, in order finally to obtain the statement 500 about the tube status or residual yarn winding status of the spinning cop tube 6 examined. To this end, the extracted characteristics are compared specifically with the expected characteristics of an abstract ideal. As an alternative or in addition, some contours can be compared with the contours of an existing "learning" cop tube. A curved rounded feature classified as a straight line, for instance, characterizes the yarn package of a residual yarn winding. In addition, a periphery found and classified as yarn characterizes the final winding of the yarn package. A tube periphery, in contrast to a yarn package periphery, has to be a straight line. If in addition no peripheries classified as yarn are extracted, then the tube in question is accordingly empty. Conversely, if corresponding peripheries classified as yarn are present in addition to a straight periphery of a tube, the tube must be one with residual yarn on it.

The concluding analysis 400 thus reliably provides a statement as to whether the specimen 6 being examined is in fact an empty tube, a tube with unusable residual yarn, or a tube with a reusable winding residue, so that, as has already been explained above, the thusly-obtained information of the computer 10 can be utilized to control the transport direction of the applicable spinning cop tube 6.

In conclusion, it should be noted that the apparatus and method described above for detecting residual yarns on spinning cop tubes can naturally also be used to check the contour of the spinning cop and thus to detect unevenness on the surface of the package.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method for detecting residual yarn on spinning cop tubes, comprising the steps of
   (a) exposing a spinning cop tube to light,
   (b) detecting the light reflected by the spinning cop tube,
   (c) generating two-dimensional picture signals of the spinning cop tube on the basis of the reflected light detected, including generating a picture matrix comprising picture data in digital form; and
   (d) evaluating the picture signals generated, the evaluating including performing an edge filtering of the digital picture data in order to emphasize image edges corresponding to brightness transitions in the picture matrix and assessing the presence of residual yarn on the spinning cop tube based on the edge filtering.

2. The method of claim 1, characterized in that the exposing of the spinning cop tube to light comprises exposing at least a yarn winding portion of the spinning cop tube to a stationary light source.

3. The method of claim 1, characterized in that the exposing of the spinning cop tube to light comprises exposing the spinning cop tube to diffuse light.

4. The method of claim 1, characterized in that the detecting of the light reflected by the spinning cop tube is performed while the spinning cop tube is in transport motion.

5. The method of claim 1, characterized in that the evaluating of the picture signals comprises evaluating whether the spinning cop tube is empty or contains a residual yarn that can be reused or contains a residual yarn that cannot be reused.

6. The method of claim 1, characterized in that the evaluating of the picture signals comprises storing the digital picture data in memory pixel by pixel in an evaluation computer and performing the evaluating thereof by means of a computer program executed by the evaluation computer.

7. The method of claim 1, characterized in that, before performing the edge filtering, performing a contrast enhancement of the digital picture data, squaring pixel by pixel the picture matrix corresponding to the digital picture data and adding the squared picture matrix to the original picture matrix.

8. The method of claim 1, characterized in that the edge filtering includes performing Sobel's filter algorithm and then binarizing the edge filtered digital picture data in order to segment the edges contained in the digital picture data.

9. The method of claim 8, characterized in that the evaluating further comprises thinning the image edges obtained by the edge filtering and, after the edge filtering and binarizing, performing an erosion of the binarized picture matrix corresponding to the digital picture data and determining the difference between the picture matrix obtained by the erosion and the edge-filtered binarized picture matrix.

10. The method of claim 1, characterized in that, after the edge filtering, performing an edge tracing of the filtered picture matrix in order to ascertain contour edges in the picture matrix.

11. The method of claim 10, characterized in that the edge tracing includes performing a Freeman chain code.

12. The method of claim 1, characterized in that the evaluating comprises evaluating the contour of the spinning cop tube in order to ascertain non-uniformities on a yarn winding surface of the spinning cop tube.

13. An apparatus for detecting residual yarn on spinning cop tubes, comprising
   (a) at least one light source for exposing a spinning cop tube to light,
   (b) a picture-taking device for detecting the light reflected by the spinning cop tube, the picture-taking device being arranged for generating two-dimensional picture signals of the spinning cop tube on the basis of the reflected light detected, including generating a picture matrix comprising picture data in digital form; and
   (c) means for evaluating the picture signals generated by the picture-taking device in order to assess the presence of residual yarn on the spinning cop tube, the picture evaluation means including means for edge filtering of the digital picture data in order to emphasize image edges corresponding to brightness transitions in the picture matrix.

14. The apparatus of claim 13, characterized in that the light source is mounted in stationary form and is arranged to expose at least a yarn-winding portion of the spinning cop tube.

15. The apparatus of claim 13, characterized in that the at least one light source exposes the spinning cop tube to diffuse light.

16. The apparatus of claim 13, characterized in that the at least one light source includes a plurality of ultra-bright light-emitting diodes which emit light in different colors and are disposed mixed in matrix fashion.

17. The apparatus of claim 13, characterized in that the at least one light source includes white light-emitting diodes.

18. The apparatus of claim 13, characterized in that the at least one light source includes a diffuser disposed between the at least one light source and the spinning cop tube for controlling the light-output by the light source.

19. The apparatus of claim 13, characterized in that the at least one light source includes a plurality of light sources arranged laterally of the spinning cop tube, each of the light sources having a plurality of light-emitting diodes arranged in a matrix and disposed to prevent total reflection of their light output to the picture-taking device.

20. The apparatus of claim 13, characterized in that the picture-taking device comprises a CCD video camera connected with a picture converter for converting the picture signal furnished by the CCD video camera into the digital picture data.

21. The apparatus of claim 20, characterized in that the CCD video camera comprises a color camera, and the picture converter is adapted to convert the picture signal of the color camera into digital picture data that correspond to different shades of gray.

22. The apparatus of claim 20, characterized in that the CCD video camera comprises a black and white camera adapted to produce a picture signal corresponding to different shades of gray.

23. The apparatus of claim 20, characterized in that the CCD video camera is oriented in a disposition rotated 90 degrees about its optical axis for detecting the light reflected by the spinning cop tube.

24. The apparatus of claim 13, characterized in that the picture-taking device comprises a digital still camera for detecting the light reflected from the spinning cop tube and for generating and delivering the digital picture data to the evaluation means.

25. The apparatus of claim 13, characterized in that the picture-taking device comprises optical distortion means which adapt the ratio of the length to width of the spinning cop tube to the gate of the picture-taking device.

26. The apparatus of claim 25, characterized in that the optical distortion means include at least one of a concave mirror and a cylindrical optical element.

27. The apparatus of claim 13, characterized in that the evaluation means is adapted to generate information as to whether the spinning cop tube is empty or contains a reusable residual yarn or contains a residual yarn that cannot be reused based upon the edges emphasized by the edge filtering means.

28. The apparatus of claim 13, characterized in that the evaluation means comprises a computer for storing the digital picture data of the picture-taking device in memory in vector fashion for digital picture processing.

29. The apparatus of claim 13, characterized in that the evaluation means comprises means for emphasizing the contrast of the digital picture matrix, including means for squaring the picture matrix corresponding to the digital picture data of the picture-taking device in pixel form and adding the squared picture matrix to the original picture matrix.

30. The apparatus of claim 13, characterized in that the edge filtering means comprises means for performing Sobel's filter algorithm on the picture matrix.

31. The apparatus of claim 13, characterized in that the evaluation means comprises means for thinning the edges contained in the picture matrix, including means for binarizing the picture matrix produced by the edge filtering means, performing an erosion thereon, and determining a difference between the picture matrix obtained by the erosion and the binarized picture matrix.

32. The apparatus of claim 13, characterized in that the evaluation means comprises means for performing an edge tracing by a Freeman chain code to ascertain contour edges contained in the filtered picture matrix.

* * * * *